United States Patent [19]

Sokoloff

[11] Patent Number: 5,533,989
[45] Date of Patent: * Jul. 9, 1996

[54] FLUID SHIELD

[76] Inventor: Daniel O. Sokoloff, 1000 45th St., West Palm Beach, Fla. 33407

[*] Notice: The portion of the term of this patent subsequent to Sep. 28, 2010, has been disclaimed.

[21] Appl. No.: 127,974

[22] Filed: Sep. 28, 1993

Related U.S. Application Data

[63] Continuation of Ser. No. 679,434, Apr. 2, 1991, Pat. No. 5,248,307.

[51] Int. Cl.$^6$ .................................................. A61M 1/00
[52] U.S. Cl. ........................ 604/327; 128/767; 604/317; 604/344
[58] Field of Search .................................. 604/317, 327, 604/332, 337–344, 349; 128/760, 767, 842, 844, 849, 850, 917, 846, 837; 4/144.1–149.4; 73/864.13; D24/224; 600/21

[56] References Cited

U.S. PATENT DOCUMENTS

| | | | |
|---|---|---|---|
| 2,385,876 | 10/1945 | Moorhead | 604/332 |
| 2,448,938 | 9/1948 | Wayne | 604/317 |
| 2,577,345 | 12/1951 | McEwen . | |
| 3,169,522 | 2/1965 | Monett | 128/837 |
| 3,714,830 | 2/1973 | Keir | 73/864.63 |
| 3,865,109 | 2/1975 | Elmore et al. . | |
| 3,920,179 | 11/1975 | Hall | 4/144.2 |
| 4,520,815 | 6/1985 | Marinoff . | |
| 4,676,244 | 6/1987 | Enstrom . | |
| 4,755,177 | 7/1988 | Hill . | |
| 4,769,858 | 9/1988 | Gamm et al. | 4/144.3 |
| 4,808,174 | 2/1989 | Sorkin | 604/349 |
| 4,889,117 | 12/1989 | Stevens . | |
| 4,892,530 | 1/1990 | Steer . | |
| 4,990,154 | 2/1991 | Brown et al. . | |
| 5,010,902 | 4/1991 | Rambo et al. | 128/846 |
| 5,248,307 | 7/1993 | Sokoloff | 604/317 |

*Primary Examiner*—Robert A. H. Clarke
*Attorney, Agent, or Firm*—Quarles & Brady

[57] ABSTRACT

A fluid shield for retarding the spraying and lateral leakage of body fluids from a pressurized anatomical structure includes a transparent flexible shield body terminating in a rim which defines an opening to the interior of the shield body. The rim is adapted to securely engage various body contours surrounding the structure so as to align the opening with the structure. The rim can be secured by adhesives or by manual pressure. The shield body can be penetrable by a surgical instrument for incising the structure, and fluids released from the ruptured structure are captured by the shield body for subsequent disposal. The shield body can be conveniently stored in a compressed stack disposed in a dispensing container. The outer surface of the rim can be textured to pull the next lower fluid shield of the compressed stack partially out of the dispensing container for subsequent removal.

8 Claims, 4 Drawing Sheets

FLUID SHIELD

This is a continuation of application Ser. No. 07/679,434 filed Apr. 2, 1991, now U.S. Pat. No. 5,248,307.

FIELD OF THE INVENTION

The invention relates to surgical apparatus. More particularly, the invention relates to surgical apparatus for controlling and containing the spraying and spreading of body fluids emitted by fluid containing cutaneous lesions or similar structures.

BACKGROUND OF THE INVENTION

It is well known that fluids contained in cutaneous lesions, such as sebaceous cysts, can be the source of various communicable diseases. The health risks attendant to contact with these fluids have been especially heightened with the discovery that the disease carriers transferable by these fluids include the HIV virus associated with Acquired Immune Deficiency Syndrome (AIDS).

Many health service providers, particularly dermatologists, surgeons, general practitioners and pediatricians are frequently exposed to the risk of contact with these fluids when performing surgical operations on cysts or other structures that contain body fluids under pressure. For example, the lancing of an inflamed sebaceous cyst, containing pressurized fluids, typically results in the forceful spraying of the fluids upon incision. Without adequate safeguards, the released fluids can spray onto the physician or attending nurses.

One known method for retarding the spray of these pressurized fluids includes loosely covering the structure with gauze padding, cloth or the like and performing the lancing procedure beneath this cover. This method is disadvantageous because the opaque cover blocks the surgeon's view of the operation.

Further, this covering method does not prevent the lateral leakage of the released fluids. The leaked fluids must be subsequently wiped away from the surrounding body surface and any fixtures to which the fluids may have traveled.

SUMMARY OF THE INVENTION

It is an object of the invention to provide a convenient fluid shield to retard the spraying of pressurized fluids from a cutaneous lesion or similar structure.

It is another object of the invention to provide a fluid shield which does not block the view of a surgeon performing an incision and drainage of a pressurized lesion.

It is still another object of the invention to provide a fluid shield which further prevents lateral leakage of fluids from the lesion during drainage.

It is a further object of the invention to provide a compact and disposable fluid shield for retarding the spraying and lateral leakage of fluids from a pressurized lesion.

It is a still further object of the invention to provide a fluid shield for retarding the spraying and lateral leakage of fluids from a pressurized lesion which is adaptable to both hair bearing and hairless body surfaces of various contours.

It is a yet further object of the invention to provide a fluid shield which easily encloses the drained fluids to facilitate safe disposal.

It is a still further object of the invention to provide a convenient and compact method of storing and dispensing fluid shields for retarding the spraying and leakage of fluids from a pressurized lesion.

These and other objects of the invention are achieved by a fluid shield having a shield body for receiving fluids emitted by a pressurized cutaneous or subcutaneous anatomical structure, such as cyst. The shield body terminates in a rim which defines an opening to the interior of the shield body. The rim is secured to the body surface surrounding the lesion so that fluids sprayed from the lesion are captured and collected in the shield body. The rim can also be sealingly secured to the body surface so that fluids subsequently drained from the lesion are prevented from leaking laterally past the rim.

The shield body is preferably made of a transparent material so that the lesion can be clearly seen through the shield body. The shield body can be made of a sufficiently rigid material so that the shield body extends outwardly from the opening when empty. The shield can also be sufficiently flexible so that the shield body sags downwardly under the weight of fluid received from the sore, thereby collecting the fluid in a localized pool.

The shield body can be constructed to form a bulbous sack which tapers to a neck portion adjacent the rim. This construction allows the shield body to be pinched or twisted off at the neck portion after drainage to sealingly enclose the drained fluids for safe disposal.

The rim of the fluid shield is preferably more rigid than the remainder of the shield body. This relatively rigid rim can be sealingly engaged to the body surface surrounding the lesion by adhesives. Further, the rim is constructed to adapt to the variety of anatomical site contours which may be presented. In hairy areas of the body, where adhesives do not perform as well, the rim can be formed as a radial flange to permit manual pressure to secure the rim to the surrounding body surface.

Although the shield body can be used to manipulate a rupture in the lesion through the shield body surface, the shield body can also be punctured by a surgical instrument, such as a scalpel, for incising the pressurized lesion. Preferably, the material of the shield body is selected so that the material merely separates to receive the scalpel and does not further rupture away from the location of the scalpel insertion. To reduce manufacturing costs of the fluid shield, a substantial portion of the shield body can be constructed of a relatively less penetrable material, and a reinforced puncturing patch can be provided to receive the incising surgical instrument.

The flexible fluid shield can be conveniently stored in a compressed stack for dispensing in a dispensing container. The compressed fluids shields can be individually pulled from an aperture in the dispensing container. Additionally, the rim surface of the fluid shield can be textured so as to pull a next lower fluid shield partially through the dispensing aperture as the dispense fluids shield is withdrawn.

The fluid shield of the invention reliably and conveniently retards the spraying and lateral leakage of potentially contaminated fluids from a pressurized lesion without blocking the surgeon's view of the operation. Additionally, the fluid shield of the invention is convenient to use in an office environment because it can be dispensed from a containerized stack and manufactured to be disposable.

BRIEF DESCRIPTION OF THE DRAWINGS

A better understanding of the invention can be gained from a reading of the following detailed description in conjunction with the associated drawings, in which.

DETAILED DESCRIPTION OF THE PREFERRED EMBODIMENTS

The invention relates to a fluid shield for retarding the spraying and leakage of fluids from a pressurized lesion or similar structure. The fluid shield can be used in conjunction with incisional procedures on cutaneous or subcutaneous structures, such as sebaceous or other cysts, as well as vascular and other pressurized anatomical structures.

Figure 1:
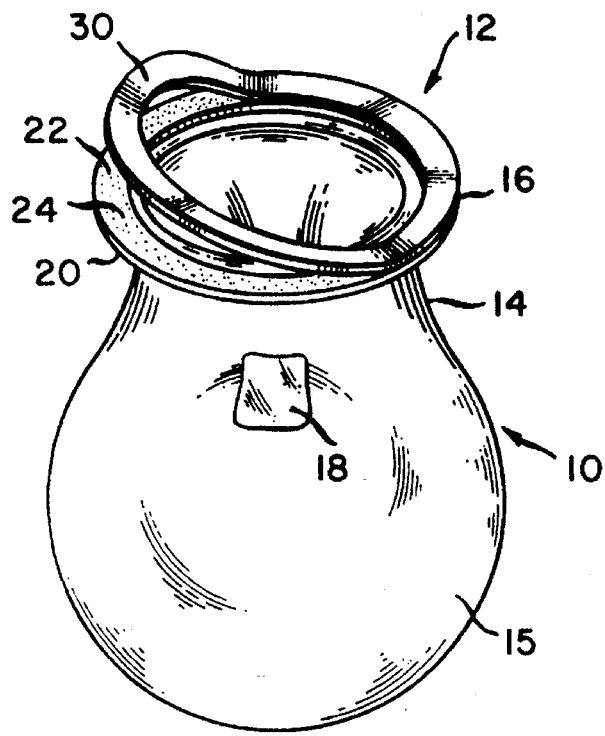
FIG. 1 is a perspective view taken from above of a preferred fluid shield of the invention.
Figure 2:
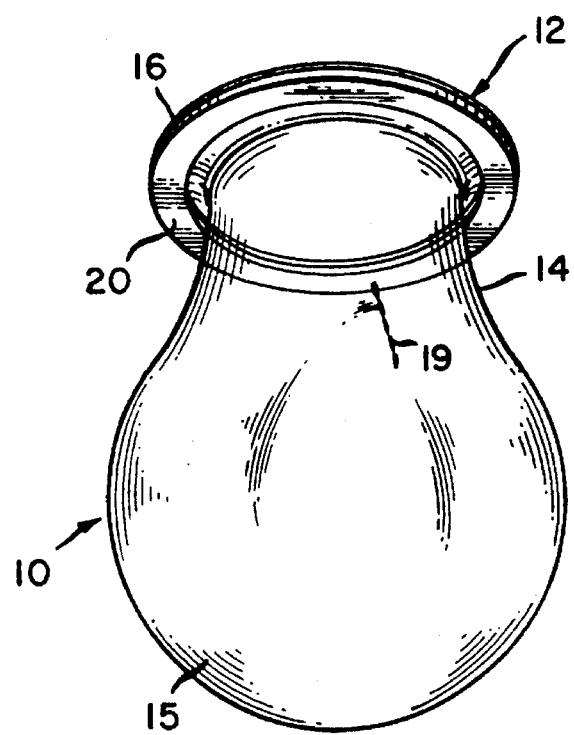
FIG. 2 is a perspective view taken from below of the fluid shield shown in FIG. 1.
Figure 3:
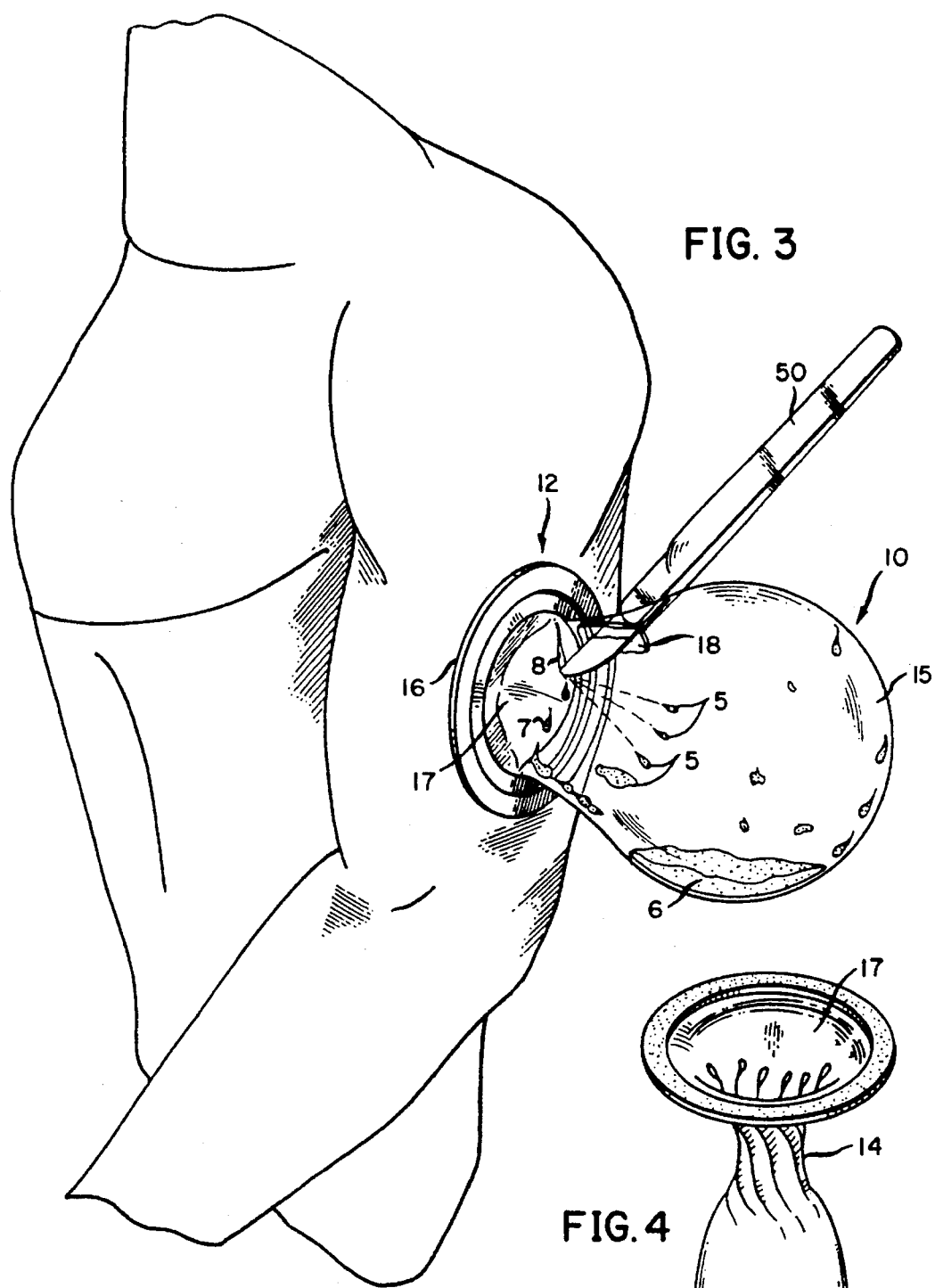
FIG. 3 shows the preferred fluid shield in one mode of operation.

Referring to FIGS. 1–3, the fluid shield includes a shield body 10 having a shield surface terminating in a rim 12. The rim defines an opening 17, which is preferably circular but can be formed in other geometric shapes. The opening 17 permits the passage of fluids into the interior of the shield body 10. During operation, the rim 12 is applied to the body surface surrounding the lesion 8 so that the lesion 8 is aligned with the opening 17 (FIG. 3).

The shield body 10 is preferably constructed of a transparent material to permit viewing of the fluid containing structure through the shield body 10. Alternatively, the shield body 10 can be constructed of a colored, translucent material.

The shield body 10 can be constructed of a sufficiently rigid material so that the shield body 10 extends substantially transversely from the body surface surrounding the lesion 8. The material of the shield body 10 is preferably sufficiently flexible to sag downwardly under the weight of the collective fluid 5 to form a collection pool 6 in the shield body 10.

Figure 4:
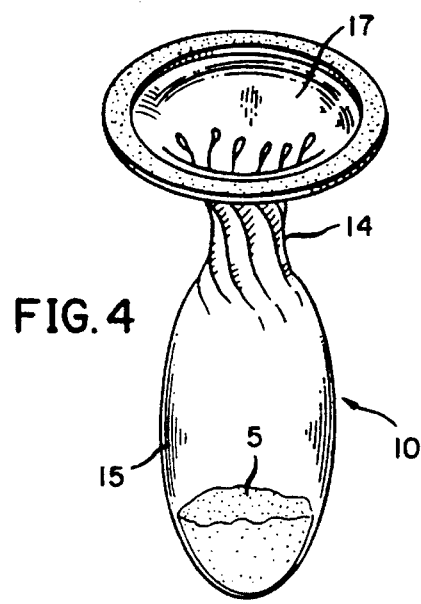
FIG. 4 shows the preferred fluid shield in a second mode of operation.

In the preferred embodiment, the shield body is formed by a bulbous sack 15 which tapers to a neck portion 14 adjacent the rim 12. The tapered neck 14 can be pinched or twisted to close the bulbous sack 15 after drainage of fluids 5 from the sore 8 to sealingly enclose the fluids 5 for disposal (FIG. 4).

Preferably, the rim 12 substantially sealingly engages the body surface surrounding the lesion 8 to prevent leakage of fluids from the lesion 8 outside the perimeter 16 of the rim 12. The rim 12 can be sealingly engaged to the body surface surrounding the lesion 8 in various ways. Preferably, the rim 12 provides a contact surface 22 having adhesives 24 for temporarily adhering to the body surface during drainage of fluids 5 from the lesion 8. Prior to use, the adhesive surface 24 can be shielded by a peelable cover 30.

Figure 5:
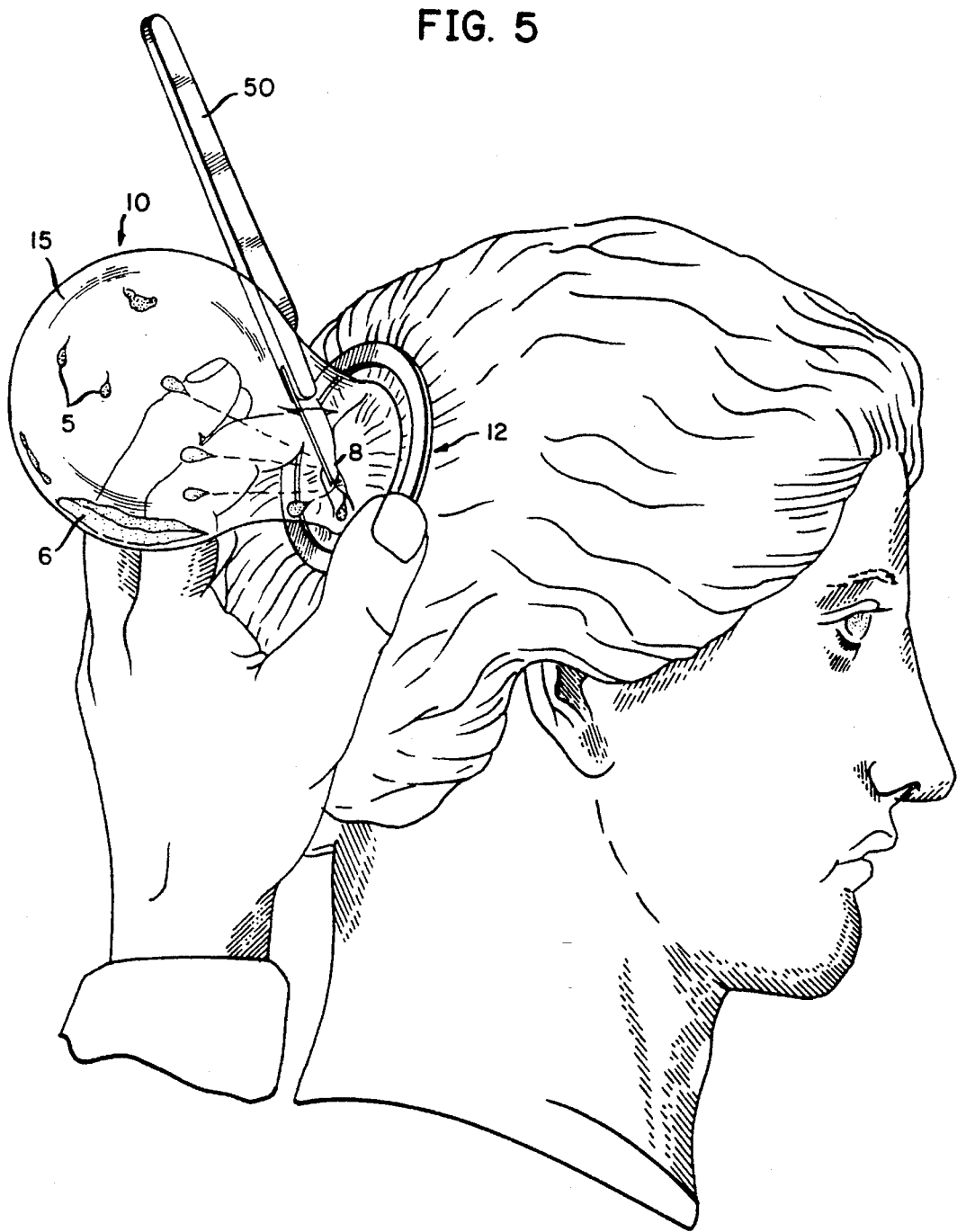
FIG. 5 shows a preferred application of the fluid shield to a hairy body surface.

In hair covered areas of a body, where the adhesives 24 might not provide an adequate sealing engagement of the rim 12, the rim 12 can be sealingly secured to the area surrounding the lesion 8 by manual pressure. Preferably, the rim 12 is formed by a flange 20 extending outwardly from the opening 17 to provide a surface for application of manual pressure (FIG. 5).

The shield body 10 is preferably flexible so that manipulation of a fluid containing structure to cause rupturing of the structure can be performed through the shield body surface. Additionally, the shield body is preferably penetrable by a surgical instrument, such as a scalpel 50, for incising the lesion 8. Preferably, the shield body 10 is constructed of a material which, when punctured, will separate to receive the scalpel without further rupture away from the location of the scalpel insertion. This formed slit reduces the likelihood of expulsion of pressurized fluid 5 from the lesion 8 through the slit. To reduce manufacturing costs, the shield body 10 can be constructed of a relatively less penetrable material and include a reinforced patch 18 which readily receives the scalpel 50 without further rupture. The patch 18 can be superimposed on the shield body 10. Alternatively, the shield body 10 can be provided with a perforated or scored line 19 to receive the incising surgical instrument. (FIG. 2).

The fluid shield of the invention conveniently and reliably retards the spraying and lateral leakage of fluids 5 from a pressurized lesion 8. In operation, the fluid shield can be retrieved from a storage unit, such as a dispensing container 40, shown in FIGS. 6–8. The peelable adhesive cover 30 is removed from the adhesive contact surface 22 of the rim 12. The rim 12 is sealingly secured to the body surface surrounding the lesion 8 by adhesion of the adhesives 22 (FIG. 3) or by manual pressure (FIG. 5). The scalpel 50 accesses the lesion 8 through the shield body 10, and ruptures the lesion 8 to permit drainage of the fluids 5.

The initial pressure of the lesion 8 can cause the emitted fluids to propel outwardly with substantial force. The outward extent of this spraying is retarded by the shield body 10, which preferably directs the sprayed fluids 5 to a localized pool 6 in a lower region of the shield body 10. After the initial pressure has been released, further fluids 7 can leak laterally from the lesion 8. These leaked fluids 7 are prevented from leaking past the fluid shield by the engagement of the rim 12 with the body surface surrounding the lesion 8.

After the lesion 8 has been sufficiently drained, the fluids 5 and 7 collected in the field body 10 can be sealingly enclosed by closing the neck portion 14 of the fluid shield. When the preferred tapered neck portion 14 is employed, this neck portion 14 can be pinched closed or twisted off to containerize the drained fluids 5.

Figure 6:
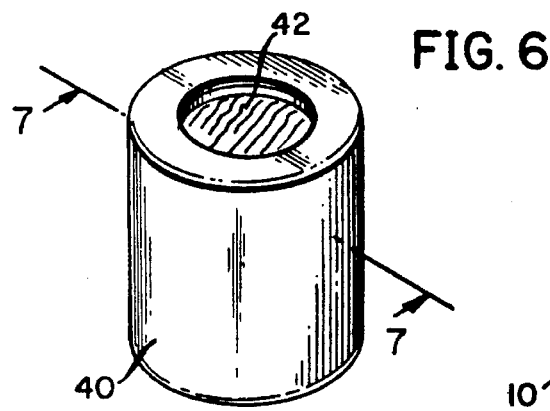
FIG. 6 is a perspective view of a preferred containerized stack of fluid shields.
Figure 7:
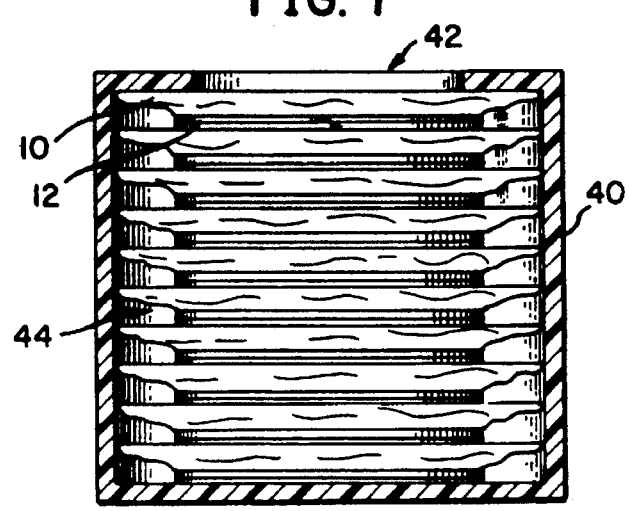
FIG. 7 is a cut-away view along line 7—7 in FIG. 6.
Figure 8:
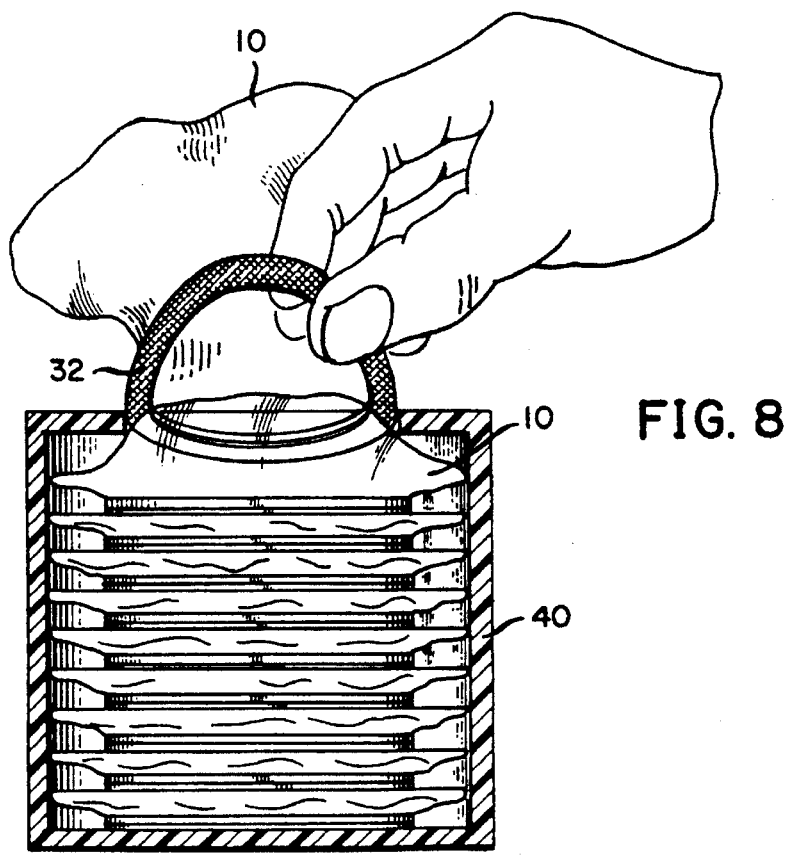
FIG. 8 shows a preferred method of dispensing the fluid shield of the invention.

In addition to a convenient and reliable construction for use and retarding the spray and lateral leakage of fluids from a pressurized lesion, the fluid shield of the invention is also adapted for convenient storage and dispensing. Referring to FIGS. 6–8, the flexible fluid shield is preferably stored in a compressed stack 44 disposed in a dispensing container 40. The stack 44 can be formed by compressing the shield body 10 into a parallel configuration with the plane of the rim 12. The compressed stack of fluid shields is stored in the dispensing container 40 for selective, individual dispensing through an aperture 42 in the dispensing container 40.

In a preferred arrangement, the rim 12 of each fluid shield is directed downwardly in the stack and adjacent to the shield body 10 of the next lower shield. The peelable cover 30, which shields the adhesive of the rim 12, can be textured on its external surface 32. As a fluid shield is withdrawn from the dispensing container through the aperture 42, the textured surface 32 pulls on the shield body 10 of the next lower fluid shield to partially pull the next lower fluid shield through the aperture 42. The partially removed fluid shield is thereby prepared for subsequent, convenient removal.

Although the fluid shield of the invention has been described above with particular reference to preferred embodiments and modes of operation, it is understood that alternative constructions and methods of employment within the scope of the invention can now be apparent to those of ordinary skill in the art. For example, the fluid shield can be constructed in a variety of sizes to accommodate fluid containing structures of different dimensions. Therefore, the scope of the invention should not be determined by the detailed description set forth above, but rather by a reasonable interpretation of the appended claims.

I claim:

1. A fluid shield for use during a medical procedure in rupturing a pressurized, fluid-containing anatomical structure to allow a user to visually observe the rupturing process, thereby improving the rupturing process and thereby protecting the user from fluid sprayed by the ruptured anatomical structure during the medical procedure, said fluid shield comprising:

a shield body having an interior for receiving fluids from the pressurized anatomical structure, said shield body having a rim defining an opening to said interior, said rim shield body having a contact surface for engaging a body surface around said structure, said shield body being constructed of a material having sufficient plasticity to extend substantially transversely from said opening in any direction when empty but penetrable by a surgical instrument for accessing and incising said structure and sufficiently flexible to enable the user to manipulate the anatomical structure with the shield, whereby said shield body retards spray of said fluids when said structure is ruptured during the medical procedure, the procedure including penetration of the shield body by a surgical instrument to form an aperture;

said shield body being constructed of a material having sufficient transparency to allow visual observation of said structure by the user through said shield body, thereby improving the rupturing process and thereby protecting the user from the fluids sprayed during the medical procedure.

2. The shield of claim 1, wherein said contact surface is adapted to substantially sealingly engage said body surface for substantially preventing said structure fluid from leaking outside a perimeter of said rim.

3. The shield of claim 1, wherein said rim is made of a material relatively more rigid than material of the shield body.

4. The shield of claim 1, further comprising an adhesive on said contact surface of said rim for temporarily adhering said rim to said body surface during transfer of fluid from said structure to said shield body.

5. The shield of claim 1, wherein said rim is an annular flange extending outwardly from a perimeter of said opening for permitting manual pressure on said flange to secure said rim to said body surface.

6. The fluid shield of claim 1, wherein said shield bottom includes an enlarged portion axially tapering to a neck portion connected to said rim, said neck portion being axially shorter than said enlarged portion.

7. The shield of claim 6, wherein said shield body is a flexible sack and said enlarged portion is bulbous.

8. The fluid shield of claim 1, wherein the interior of the shield body in unobstructed toward the opening and is free from any obstructing structure extending inwardly from interior peripheral surfaces of the shield body and rim, whereby visual and physical access to the anatomical structure through the shield body is unobstructed.

* * * * *